United States Patent [19]

Hunziker

[11] Patent Number: 5,206,023
[45] Date of Patent: Apr. 27, 1993

[54] METHOD AND COMPOSITIONS FOR THE TREATMENT AND REPAIR OF DEFECTS OR LESIONS IN CARTILAGE

[75] Inventor: Ernst B. Hunziker, Riedholz, Switzerland

[73] Assignee: Robert F. Shaw, San Francisco, Calif.

[21] Appl. No.: 648,274

[22] Filed: Jan. 31, 1991

[51] Int. Cl.⁵ .......................... A61F 2/02; A61K 37/22; C07K 15/06; C09H 3/02
[52] U.S. Cl. .................... 424/423; 424/422; 424/424; 424/425; 424/426; 424/450; 424/484; 424/489; 424/499; 514/2; 514/8; 514/944; 514/953; 514/965; 530/350; 530/351; 530/353; 530/354; 530/356; 530/840
[58] Field of Search .............. 424/422, 423, 424, 425, 424/426, 450, 484, 489, 499; 514/2, 8, 944, 953, 965; 530/350, 351, 353, 354, 356, 840

[56] References Cited

U.S. PATENT DOCUMENTS

| | | | |
|---|---|---|---|
| 3,966,908 | 6/1976 | Balassa | 424/95 |
| 4,346,709 | 8/1982 | Schmidtt | 128/260 |
| 4,418,691 | 12/1983 | Yannas et al. | 128/156 |
| 4,604,234 | 8/1986 | Fujii et al. | 514/2 |
| 4,609,551 | 9/1986 | Caplan et al. | 424/95 |
| 4,638,045 | 1/1987 | Kohn et al. | 530/323 |
| 4,642,120 | 2/1987 | Nevo et al. | 623/16 |
| 4,774,228 | 9/1988 | Seyedin et al. | 514/21 |
| 4,774,322 | 9/1988 | Seyedin et al. | 530/353 |
| 4,785,079 | 11/1988 | Gospodarowicz et al. | 530/399 |
| 4,810,691 | 3/1989 | Seyedin et al. | 514/2 |
| 4,843,063 | 6/1989 | Seyedin et al. | 514/2 |
| 4,846,835 | 7/1989 | Grande | 623/11 |
| 4,886,747 | 12/1989 | Derynck et al. | 435/69.4 |
| 4,917,893 | 4/1990 | Okada et al. | 424/423 |
| 4,944,948 | 7/1990 | Uster et al. | 424/450 |
| 4,950,483 | 8/1990 | Ksander et al. | 424/422 |
| 4,952,403 | 8/1990 | Vallee et al. | 424/422 |
| 4,952,404 | 8/1990 | Vallee et al. | 424/422 |
| 4,975,526 | 12/1990 | Kuberasampath et al. | 530/350 |

FOREIGN PATENT DOCUMENTS

| | | |
|---|---|---|
| 128849A1 | 12/1984 | European Pat. Off. |
| 293785A2 | 12/1988 | European Pat. Off. |
| 374044A2 | 6/1990 | European Pat. Off. |
| 376785A2 | 7/1990 | European Pat. Off. |
| 167263B1 | 8/1990 | European Pat. Off. |
| 8607595 | 12/1986 | PCT Int'l Appl. |
| 8805788 | 8/1988 | PCT Int'l Appl. |
| 8907425 | 8/1989 | PCT Int'l Appl. |
| 8907613 | 8/1989 | PCT Int'l Appl. |
| 8909787 | 10/1989 | PCT Int'l Appl. |
| 8909788 | 10/1989 | PCT Int'l Appl. |
| 8912101 | 12/1989 | PCT Int'l Appl. |
| 9000060 | 1/1990 | PCT Int'l Appl. |
| 9009166 | 8/1990 | PCT Int'l Appl. |
| 9009783 | 9/1990 | PCT Int'l Appl. |
| 9010018 | 9/1990 | PCT Int'l Appl. |
| 9013317 | 11/1990 | PCT Int'l Appl. |
| 9104267 | 4/1991 | PCT Int'l Appl. |

OTHER PUBLICATIONS

"Accelerated Wound Repair, Cell Proliferation, and Collagen Accumulation are Produced by Cartilage-Derived Growth Factor", Davidson et al., J. Cell Biol., 100(4), 1219-27 (Abstact only).

(List continued on next page.)

Primary Examiner—Thurman K. Page
Assistant Examiner—Carlos Azpuru
Attorney, Agent, or Firm—James F. Haley, Jr.; Jane A. Massaro

[57] ABSTRACT

Methods and compositions are provided for the treatment and repair of defects or lesions in the cartilage of humans and other animals. The defect or lesion in the cartilage may be first treated with an enzyme to remove proteoglycans from the defect area. To induce cartilage formation, the defect is filled or otherwise dressed with a biodegradable matrix having pores sufficiently large to allow repair cells to populate the matrix. The matrix filling the defect contains a proliferation agent at a concentration sufficient to stimulate proliferation of repair cells and a transforming factor in an appropriate delivery system to release the transforming factor at a concentration sufficient to transform repair cells in the matrix and defect area into cartilage-producing chondrocytes. The matrix may also contain a chemotactic agent to attract repair cells. The entire treatment may be carried out in a single arthroscopic or open surgical procedure.

24 Claims, No Drawings

OTHER PUBLICATIONS

"Experimental Investigations of Osteogenesis and Chondrogenesis by Implant of BMP-Fibrin Glue Mixture", Nippon Sei Keigeka Gakkai Zasshi, 64(9), 824-34.

Burgess, A. W., "Hemopoietic Growth Factors: Structure and Receptor Interactions", In *Growth factors in biology and medicine*, pp. 148-168 (London: Pitman, 1985).

Callahan, M. et al., "The PDGF-Inducible 'Competence Genes': Intracellular Mediators of the Mitogenic Response", in *Growth factors in biology and medicine*, pp. 87-97 (London: Pitman, 1985).

Cheifetz, S. et al., "The Transforming Growth Factor-$\beta$ System, a Complex Pattern of Cross-Reactive Ligands and Receptors", *Cell*, 48, pp. 409-415 (Feb. 13, 1987).

Cuevas, P. et al., "Basic Fibroblast Growth Factor (FGF) Promotes Cartilage Repair In Vivo", *Biochem. Biophys. Res. Commun.*, 156, pp. 611-618 (Oct. 31, 1988).

Dexter, T. M. et al., "The Role of Hemopoietic Cell Growth Factor (Interleukin 3) in the Development of Hemopoietic Cells", in *Growth factors in biology and medicine*, pp. 129-147 (London: Pitman, 1985).

Dijke, P. et al., "Growth Factors for Wound Healing", *Biotech.*, 7, pp. 793-798 (Aug. 1989).

Gimenez-Gallego, G. et al., "Human Brain-Derived Acidic and Basic Fibroblast Growth Factors: Amino Terminal Sequences and Specific Mitogenic Activities", *Biochem. Biophys. Res. Commun.*, 135, pp. 541-548 (Mar. 13, 1986).

Heller, J. et al., "Use of Bioerodible Polymers in Self-Regulated Drug Delivery Systems", in *Controlled Release Technology* pp. 172-187 (Washington, D.C.: American Chemical Society, 1987).

Huang, J. S. et al., "Role of Growth Factors in Oncongenesis: Growth Factor-Proto-Oncogene Pathways of Mitogenesis", in *Growth factors in biology and medicine*, pp. 46-65 (London: Pitman, 1985).

Hutchinson, F. G. et al., "Design of Biodegradable Polymers for Controlled Release", in *Drug Delivery Systems*, pp. 106-119 (Chichester: Ellis Horwood, 1987).

Ignotz, R. A. et al., "Transforming Growth Factor-$\beta$-Stimulates the Expression of Fibronectin and Collagen and Their Incorporation into the Extracellular Matrix", *J. Biol. Chem.*, 261, pp. 4337-4345 (Mar. 25, 1986).

Kim, S. et al., "Preparation of Multivesicular Liposomes", *Biochim. Biophys. Acta*, 728, pp. 339-348 (1983).

Moore, A. R. et al., "The Chemotactic Properties of Cartilage Glycosaminoglycans for Polymer Pronuclear Neutrophils", *Int. J. Tiss. Reac.*, XI pp. 301-307 (1989).

Postelthwaite, A. E. et al., "Stimulation of the Chemotactic Migration of Human Fibroblasts by Transforming Growth Factor $\beta$", *J. Exp. Med.*, 165, pp. 351-256 (Jan. 1987).

Ray, N. et al., "Implantable Osmotically Powered Drug Delivery Systems", in *Drug Delivery Systems*, pp. 120-138 (Chichester: Ellis Horwood, 1987).

Rizzino, A., "Transforming Growth Factor-$\beta$: Multiple Effects on Cell Differentiation and Extracellular Matrices", *Develop. Biol.*, 130, pp. 411-422 (1988).

Roberts, A. B. et al., "The Transforming Factor-$\beta$s", in *Peptide Growth Factors and Their Receptors I*, pp. 419-472 (Berlin: Springer-Verlag, 1990).

Ruoslahti, E. et al., "Ary-Gly-Asp: A Versatile Cell Recognition Signal", *Cell*, 44, pp. 517-518 (Feb. 28, 1986).

Seyedin, S. M. et al., "Purification and Characterization of Two Cartilage-Including Factors from Bovine Demineralized Bone", *Proc. Natl. Acad. Sci. USA*, 82, pp. 2267-2271 (Apr. 1985).

Seyedin, S. M. et al., "Cartilage-Including Factor A, Apparent Identity to Transforming Growth Factor-$\beta$", *J. Biol. Chem.*, 261, pp. 5693-5695 (May 5, 1986).

Seyedin, S. M. et al., "Cartilage-Inducing Factor-$\beta$ is a Unique Protein Structurally and Functionally Related to Transforming Growth Factor-$\beta$", *J. Biol. Chem.*, 262, pp. 1946-1949 (Feb. 15, 1987).

Sporn, M. B. et al., "Some Recent Advances in the Chemisry and Biology of Transforming Growth Factor-$\beta$", *J. Cell. Biol.*, 105, pp. 1039-1045 (Sep. 1987).

Wahl, S. M. et al., "Transforming Growth Factor Type $\beta$ Induces Monocyte Chemotaxis and Growth Factor Production", *Proc. Natl. Acad. Sci. USA*, 84, pp. 5788-5792 (Aug. 1987).

Zapf, J. et al., "In Vivo Effects of the Insulin-Like Growth Factors (IGFs) in the Hypophysectomized Rat: Comparison with Human Growth Hormone and the Possible Role of the Specific IGF Carrier Proteins", In *Growth factors in biology and medicine*, pp. 169-186 (London: Pitman, 1985).

METHOD AND COMPOSITIONS FOR THE TREATMENT AND REPAIR OF DEFECTS OR LESIONS IN CARTILAGE

TECHNICAL FIELD OF THE INVENTION

This invention relates to the treatment and repair of defects or lesions in cartilage. More specifically, this invention relates to methods for treating defects or lesions (used interchangeably herein) in cartilage and to compositions comprising a biodegradable matrix containing one or more proliferating agents to promote proliferation of repair cells to form new stable cartilage tissue. The compositions and methods of this invention are particularly useful in the treatment of osteoarthritis and other diseases and traumas that produce cartilage injury.

BACKGROUND ART

Joints are one of the common ways bones in the skeleton are connected. The ends of normal articulated bones are covered by articular cartilage tissue, which permits practically frictionless movement of the bones with respect to one another [L. Weiss, ed., Cell and Tissue Biology (Munchen: Urban and Schwarzenburg, 1988) p. 247].

Articular cartilage is characterized by a particular structural organization. It consists of specialized cells (chondrocytes) embedded in an intercellular material (often referred to in the literature as the "cartilage matrix") which is rich in proteoglycans, collagen fibrils of predominantly type II, other proteins, and water [Buckwalter et al., "Articular Cartilage: Injury and Repair," in Injury and Repair of the Musculoskeletal Soft Tissues (Park Ridge, Ill.: American Academy of Orthopaedic Surgeons Symposium, 1987) p. 465]. Cartilage tissue is neither innervated nor penetrated by the vascular or lymphatic systems. However, in the mature joint of adults, the underlying subchondral bone tissue, which forms a narrow, continuous plate between the bone tissue and the cartilage, is innervated and vascularized. Beneath this bone plate, the bone tissue forms trabeculae, containing the marrow. In immature joints, articular cartilage is underlined by only primary bone trabeculae. A portion of the meniscal tissue in joints also consists of cartilage whose make-up is similar to articular cartilage [Beaupre, A. et al., Clin. Orthop. Rel. Res., pp. 72-76 (1986)].

Two types of defects or lesions are recognized in cartilage tissue, i.e., full-thickness defects and superficial defects. These defects differ not only in the extent of physical damage to the cartilage, but also in the nature of the repair response each type of lesion can elicit.

Full-thickness defects extend to the subchondral bone and can cause severe pain since the bone plate contains sensory nerve endings. Such defects generally arise from severe trauma or during the late stages of degenerative joint disease, such as osteoarthritis. Full-thickness defects may, on occasion, lead to bleeding and the induction of a repair reaction from the subchondral bone [Buckwalter et al., "Articular Cartilage: Composition, Structure, Response to Injury, and Methods of Facilitating Repair," in Articular Cartilage and Knee Joint Function: Basic Science and Arthroscopy (New York: Raven Press, 1990) pp. 19-56]. The repair tissue formed is a vascularized fibrous type of cartilage with insufficient biomechanical properties, and does not persist on a long-term basis [Buckwalter et al. (1990), supra].

Superficial defects in the articular cartilage tissue are restricted to the cartilage tissue itself. Such defects are notorious because they do not heal and show no propensity for repair reactions.

These defects may appear as fissures, divots, or clefts in the surface of the cartilage, or they may have a "crabmeat" appearance in the affected tissue. They contain no bleeding vessels (blood spots) such as are seen in full-thickness defects. Superficial defects may have no known cause, but often they are the result of mechanical derangements which lead to a wearing down of the cartilaginous tissue. Mechanical derangements may be caused by trauma to the joint, e.g., a displacement of torn meniscus tissue into the joint, meniscectomy, a laxation of the joint by a torn ligament, malalignment of joints, or bone fracture, or by hereditary diseases. Superficial defects are also characteristic of early stages of degenerative joint diseases, such as osteoarthritis. Since the cartilage tissue is not innervated [Ham's Histology (9th ed.) (Philadelphia: J.B. Lippncott Co. 1987), pp. 266-272]or vascularized, superficial defects are not painful. However, although painless, superficial defects do not heal and often degenerate into full-thickness defects.

It is generally believed that because articular cartilage lacks a vasculature, damaged cartilage tissue does not receive sufficient or proper stimuli to elicit a repair response [Webber et al., "Intrinsic Repair Capabilities of Rabbit Meniscal Fibrocartilage: A Cell Culture Model", (30th Ann. Orthop. Res. Soc., Atlanta, Feb. 1984); Webber et al., J. Orthop. Res., 3, pp. 36-42 (1985)]. It is theorized that the chondrocytes in the cartilaginous tissue are normally not exposed to sufficient amounts of repair-stimulating agents such as growth factors and fibrin clots typically present in damaged vascularized tissue.

One approach that has been used to expose damaged cartilage tissue to repair stimuli involves drilling or scraping through the cartilage into the subchondral bone to cause bleeding [Buckwalter et al. (1990), supra1. Unfortunately, the repair response of the tissue to such surgical trauma is usually comparable to that observed to take place naturally in full-thickness defects that cause bleeding, viz., formation of a fibrous type of cartilage which exhibits insufficient biomechanical properties and which does not persist on a long-term basis [Buckwalter et al. (1990), supra].

A variety of growth factors have been isolated and are now available for research and biomedical applications [see e.g., Rizzino, A., Dev. Biol., 130, pp. 411–22 (1988)]. Some of these growth factors, such as transforming growth factor beta (TGF-B), have been reported to promote formation of cartilage-specific molecules, such as type II collagen and cartilage-specific proteoglycans, in embryonic rat mesenchymal cells in vitro [e.g., Seyedin et al., Proc. Natl. Acad. Sci. USA, 82, pp. 2267-71 (1985); Seyedin et al., J. Biol. Chem., 261, pp. 5693-95 (1986); Seyedin et al., J. Biol. Chem., 262, pp. 1946-1949 (1987)].

Millions of patients have been diagnosed as having osteoarthritis, i.e., as having degenerating defects or lesions in their articular cartilage. Nevertheless, despite claims of various methods to elicit a repair response in damaged cartilage, none of these treatments has received substantial application [Buckwalter et al. (1990), supra; Knutson et al., J. Bone and Joint Surg., 68-B, p.

795 (1986); Knutson et al., *J. Bone and Joint Surg.* 67-B, p. 47 (1985); Knutson et al., *Clin Orthop.*, 191, p. 202 (1984); Marquet, *Clin. Orthop.* 146, p. 102 (1980)]. And such treatments have generally provided only temporary relief. Systemic use of "chondroprotective agents" has also been purported to arrest the progression of osteoarthritis and to induce relief of pain. However, such agents have not been shown to promote repair of lesions or defects in cartilage tissue.

To date, treatment of patients suffering from osteoarthritis has been directed largely to symptomatic relief through the use of analgesics and anti-inflammatory agents. Without a treatment that will elicit repair of superficial defects in articular cartilage, the cartilage frequently wears down to the subchondral bone plate. At this phase of the disease, i.e., severe osteoarthritis, the unremitting nature of the pain and the significant compromise of function often dictates that the entire joint be excised and replaced with an artificial joint of metal and/or plastic. Some one-half million procedures comprising joint resection and replacement with an artificial joint are currently performed on knees and hips each year. [See e.g., Graves, E.J., "1988 Summary; National Hospital Discharge Survey", *Advanced Data From Vital and Health Statistics*, 185, pp. 1-12 (Jun. 19, 1990)].

There is, therefore, a need for a reliable treatment for cartilage defects which can induce repair and regeneration of stable cartilage and prevent the progression of superficial cartilage defects or lesions into severe osteoarthritis.

SUMMARY OF THE INVENTION

The present invention solves the problems referred to above by providing effective therapeutic methods and compositions to induce the repair of lesions in cartilage of humans and other animals. Use of the methods and compositions of this invention also prevents the progression of traumatic lesions and early forms of osteoarthritis which would otherwise lead to severe osteoarthritis with unremitting pain and loss of effective joint function leading to probable resection and replacement of the joint.

In general outline, the methods of this invention for repairing cartilage defects comprise filling or otherwise dressing a defect in the cartilage with a composition of this invention comprising (1) a biodegradable matrix or matrix-forming material, (2) a proliferation agent to promote the proliferation of repair cells in the matrix and defect area, and, in certain embodiments., (3) a chemotactic agent to attract repair cells to the matrix and defect area, and (4) a transforming factor in an appropriate delivery system which will release the transforming factor at an appropriate time to promote differentiation (i.e., transformation) of the repair cells in the matrix or defect area into chondrocytes which produce new stable cartilage tissue. Alternatively, the transforming factor may be added to the defect site separately at the appropriate time.

Treatment of cartilage defects can be effected during a single arthroscopic or surgical procedure using the methods of this invention. According to certain methods of this invention, after identification of the defect, the defect is treated by the steps of (1) filling the defect area with an enzyme, which degrades the proteoglycans present on the surface of the defect, (2) removing the enzyme, and (3) dressing the defect with a composition comprising a matrix, a proliferation agent, and a transforming factor in an appropriate delivery system.

DETAILED DESCRIPTION OF INVENTION

In order that the invention may be more fully understood, the following detailed description is provided. In the description the following terms are used.

Arthroscopy—as used herein, refers to the use of an arthroscope to examine or perform surgery on a joint.

Cartilage—as used herein, refers to a type of connective tissue that contains chondrocytes embedded in an intercellular material (often referred to as the "cartilage matrix") comprising fibrils of collagen (predominantly type II collagen along with other minor types, e.g., types IX and XI), various proteoglycans (e.g., chondroitinsulfate-, keratansulfate-, and dermatansulfate proteoglycans), other proteins, and water. Cartilage as used herein includes articular and meniscal cartilage. Articular cartilage covers the surfaces of the portions of bones in joints and allows movement in joints without direct bone-to-bone contact, and thereby prevents wearing down and damage to apposing bone surfaces. Most normal healthy articular cartilage is also described as "hyaline", i.e., having a characteristic frosted glass appearance. Meniscal cartilage is usually found in joints which are exposed to concussion as well as movement. Such locations of meniscal cartilage include the tempomandibular, sterno-clavicular, acromioclavicular, wrist and knee joints [*Gray's Anatomy* (New York: Bounty Books, 1977)].

Cell adhesion promoting factor—as used herein, refers to any compound or composition, including fibronectin and other peptides as small as tetrapeptides which comprise the tripeptide Arg-Gly-Asp, which mediates the adhesion of cells to extracellular material [Ruoslathi et al., *Cell*, 44, pp. 517-518 (1986)].

Chemotactic Agent—as used herein, refers to any compound or composition, including peptides, proteins, glycoproteins and glycosaminoglycan chains, which is capable of attracting cells in standard in vitro chemotactic assays [e.g., Wahl et al., *Proc. Natl. Acad. Sci. USA*, 84, pp. 5788-92 (1987); Postlewaite et al., *J. Exp. Med.*, 165, pp. 251-56 (1987); Moore et al., *Int. J. Tiss. Reac.*, XI, pp. 301-07 (1989)].

Chondrocytes—as used herein, refers to cells which are capable of producing components of cartilage tissue, e.g., type II cartilaginous fibrils and fibers and proteoglycans.

Fibroblast growth factor (FGF)—any member of the family of FGF polypeptides [Gimenez-Gallego et al., Biochem. Biophys. Res. Commun.. 135, pp. 541-548 (1986); Thomas et al., Trends Biochem. Sci., 11, pp. 81-84 (1986)] or derivatives thereof, obtained from natural, synthetic or recombinant sources, which exhibits the ability to stimulate DNA synthesis and cell division in vitro [for assays see, e.g., Giminez-Gallego et al., 1986, supra; Canalis et al., *J. Clin. Invest.*, 81, pp. 1572-1577 (1988)] of a variety of cells, including primary fibroblasts, chondrocytes, vascular and corneal endothelial cells, osteoblasts, myoblasts, smooth muscle and glial cells [Thomas et al., 1986, supra]. FGFs may be classified as acidic (aFGF) or basic (bFGF) FGF, depending on their isoelectric points (pI).

Matrix—as used herein, refers to a porous composite, solid or semi-solid biodegradable substance having pores or spaces sufficiently large to allow cells to populate the matrix. The term matrix includes matrix-forming materials, i.e., materials which can form matrices within the defect site in cartilage. Matrix-forming materials may require addition of a polymerizing agent to form a matrix, such as adding thrombin to a solution containing fibrinogen to form a fibrin matrix.

Proliferation (mitogenic) Agent—as used herein, refers to any compound or composition, including peptides, proteins, and glycoproteins, which is capable of stimulating proliferation of cells in vitro. In vitro assays to determine the proliferation (mitogenic) activity of peptides, polypeptides and other compounds are well-known in the art [see, e.g., Canalis et al., *J. Clin. Invest.*, pp. 1572–77 (1988); Gimenez-Gallego et al., *Biochem. Biophys. Res. Commun.*, 135, pp. 541–548 (1986); Rizzino, "Soft Agar Growth Assays for Transforming Growth Factors and Mitogenic Peptides", in *Methods Enzymol.*, 146A (New York: Academic Press, 1987), pp. 341–52; Dickson et al., "Assay of Mitogen-Induced Effects on Cellular Incorporation of Precursors for Scavengers, de Novo, and Net DA Synthesis", in *Methods Enzymol.*, 146A (New York: Academic Press, 1987), pp. 329–40]. One standard method to determine the proliferation (mitogenic) activity of a compound or composition is to assay it in vitro for its ability to induce anchorage-independent growth of nontransformed cells in soft agar [e.g., Rizzino, 1987, supra]. Other mitogenic activity assay systems are also known [e.g., Gimenez-Gallego et al., 1986, supra; Canalis et al., 1988, supra; Dickson et al., 1987, supra].

Repair Cell—as used herein, refers to a cell which, when exposed to appropriate stimuli, will differentiate and be transformed into a chondrocyte. Repair cells include mesenchymal cells, fibroblasts, fibroblast-like celss, macrophages, and dedifferentiated chondrocytes.

Transforming Factor—as used herein, refers to any peptide, polypeptide, protein, or any other compound or composition which induces differentiation of a repair cell into a chondrocyte. The ability of the compound or composition to induce or stimulate production of cartilage-specific proteoglycans and type II collagen by cells can be determined by in vitro assays known in the art [Seyedin et al., *Proc. Natl. Acad. Sci. USA*, 82, pp. 2267–71 (1985); Seyedin et al., *Path. Immunol. Res.*, 7, pp. 38–42 (1987)].

Transforming Growth Factor Beta (TGF-$\beta$)—any member of the family of TGF-$\beta$ polypeptides [Derynck, R. et al., *Nature*, 316, pp. 701–705 (1985); Roberts et al., "The transforming growth factor-$\beta$'s", In *Peptide growth factors and their receptors I* (Berlin: Springer Verlag, 1990), p. 419)]or derivatives thereof, obtained from natural, synthetic or recombinant sources, which exhibits the characteristic TGF-$\beta$ ability to stimulate normal rat kidney (NRK) cells to grow and form colonies in a soft agar assay [Roberts et al., 1984, supra] and which is capable of inducing transformation of repair cells into chondrocytes as evidenced by the ability to induce or stimulate production of cartilage-specific proteoglycans and type II collagen by cells in vitro [Seyedin et al., 1985, supra].

This invention relates to compositions and methods for treating defects or lesions in cartilage. The compositions of this invention comprise a biodegradable matrix having pores sufficiently large to allow repair cells to populate the matrix. The matrix also contains a proliferation agent to stimulate the proliferation of repair cells in the matrix. Preferably, the proliferation agent also serves as a chemotactic agent to attract repair cells to the matrix. Alternatively, the matrix may contain a chemotactic agent in addition to the proliferation agent.

In one preferred embodiment of this invention, the matrix also contains an appropriate concentration of a transforming factor, the transforming factor being contained within or in association with a delivery system which effects release of the transforming factor at the appropriate time to transform the proliferated repair cells in the matrix into chondrocytes which produce stable cartilage tissue. The matrix may also contain a cell adhesion promoting factor.

Matrix materials useful in the methods and compositions of this invention for filling or otherwise dressing the defect in the cartilage include fibrinogen (activated with thrombin to form fibrin in the defect or lesion), collagen, Sepharose, gelatin and any other biodegradable material which forms a matrix with pores sufficiently large to allow repair cells to populate and proliferate within the matrix and which can be degraded and replaced with cartilage during the repair process.

The matrices useful in the compositions and methods of this invention may be preformed or may be formed in situ, for example, by polymerizing compounds and compositions such as fibrinogen to form a fibrin matrix. Matrices that may be preformed include collagen (e.g., collagen sponges and collagen fleece), chemically modified collagen, gelatin beads or sponges, a gel-forming substance such as Sepharose, any other gel-forming or composite substance that is composed of a biodegradable matrix material that will fill the defect and allow repair cells to populate the matrix, or mixtures of the above.

In a preferred embodiment of this invention, the matrix is formed using a matrix-forming material, preferably a solution of fibrinogen, to which is added thrombin to initiate polymerization shortly before use. A fibrinogen concentration of 0.5–5 mg/ml of an aqueous buffer solution may be used. Preferably, a fibrinogen solution of 1 mg/ml of an aqueous buffer solution is used. Polymerization of this fibrinogen solution in the defect area yields a matrix with a pore size sufficiently large (e.g., approximately 50–200 $\mu$m) so that repair cells are free to populate the matrix and proliferate in order to fill the volume of the defect that the matrix occupies. Preferably, a sufficient amount of thrombin is added to the fibrinogen solution shortly before application in order to allow enough time for the surgeon to deposit the material in the defect area prior to completion of polymerization. Typically, the thrombin concentration should be such that polymerization is achieved within a few to several (2–4) minutes since exposure of cartilage to air for lengthy periods of time has been shown to cause damage [Mitchell et al., *J. Bone Joint Surg.*, 71A pp. 89–95 (1989)]. Excessive amounts of thrombin should not be used since thrombin has the ability to cleave growth factor molecules and inactivate them. Thrombin solutions of 10–500 units per ml, and preferably 100 units per ml, of an aqueous buffer solution may be prepared for addition to the fibrinogen solution. In a preferred embodiment of this invention, approximately 20 $\mu$l of thrombin (100 U/ml) are mixed with each ml of a fibrinogen solution (1 mg/ml) approximately 200 seconds before filling the defect. Polymerization will occur more slowly if a lower concentration of thrombin is added. It will be appreciated that the amount of thrombin solution needed to achieve fibrin polymerization within 2–4 minutes can be given only approximately, since it depends upon the environmental temperature, the temperature of the thrombin solution, the temperature of the fibrinogen solution, etc. The polymerization of the thrombin-activated matrix solution filling the defect is easily monitored by observing the thrombin-induced polymerization of an external sample of the fibrinogen solution. Preferably, in the compositions and methods of this invention, fibrin matrices are formed from autologous fibrinogen molecules, i.e., fibrinogen molecules derived from the blood of the same mammalian species as the species to be treated. Non-immunogenic fibrinogen from her species may also be used.

When collagen is used as a matrix material, sufficiently viscous solutions can be made, e.g., using Collagen-Vliess ® ("fleece") or gelatine-blood-mixtures, and there is no need for a polymerizing agent. Collagen matrices may also be used with a fibrinogen solution activated with a polymerizing agent so that a combined matrix results.

Polymerizing agents may also be unnecessary when other biodegradable compounds are used to form the matrix. For example, Sepharose solutions may be chosen that will be liquid matrix solutions at 39–42° C. and become solid (i.e., gel-like) at 35–38° C. The Sepharose should also be at concentrations such that the gel filling the cartilage defect has a mesh size to allow repair cells to freely populate the matrix and defect area.

In the compositions of this invention, one or more proliferation (mitogenic) agents may be added to the matrix solution. The proliferation agent or agents should be present in an appropriate concentration range to have a proliferative effect on repair cells in the matrix filling the defect (see Examples section). Preferably, the same agent should also have a chemotactic effect on the cells (as in the case of TGF-$\beta$); however, a factor having exclusively a proliferative effect may be used. Alternatively, to produce chemotactic cell immigration, followed by induction of cell proliferation, two different agents may be used, each one having just one of those specific effects (either chemotactic or proliferative).

Proliferation (mitogenic) agents useful in the compositions and methods of this invention for stimulating the proliferation of repair cells include transforming growth factors ("TGFs") such as TGF-$\alpha$S and TGF-$\beta$s; insulin-like growth factor ("IGF I"); acidic or basic fibroblast growth factors ("FGFs"); platelet-derived growth factor ("PDGF"); epidermal growth factor ("EGF"); and hemopoietic growth factors, such as interleukin 3 ("IL-3") [Rizzino, 1987, supra; Canalis et al., supra, 1988; *Growth factors in biology and medicine, Ciba Foundation Symposium*, 116 (New York: John Wiley & Sons, 1985); Baserga, R., ed., *Cell growth and division* (Oxford: IRL Press, 1985); Sporn, M.A. and Roberts, A.B., eds., *Peptide growth factors and their receptors*, Vols. I and II (Berlin: Springer-Verlag, 1990)]. However, these particular examples are not limiting. Any compound or composition which is capable of stimulating the proliferation of cells as demonstrated by an in vitro assay for cell proliferation is useful as a proliferation agent in this invention. Such assays are known in the art [e.g., Canalis et al., 1988, supra; Gimenez-Gallego et al., 1986, supra; Dickson et al., 1987, supra; Rizzino, 1987, supra].

Chemotactic agents useful in the compositions and methods of this invention for attracting repair cells include, for example, TGF-Bs, FGFs (acid or basic), PDGF, tumor necrosis factors (e.g., TNF-$\alpha$, TNF-$\beta$) and proteoglycan degradation products, such as glycosaminoglycan chains [Roberts et al. (1990), supra; *Growth factors in biology and medicine. Ciba Foundation Symposium*, 116 (New York, John Wiley & Sons, 1985); R. Baserga, ed., *Cell growth and division* (Oxford: IRL Press, 1985)]. Assays to determine the chemotactic ability of polypeptides and other compounds are known in the art [e.g., Postlewaite et al., 1987, supra; Wahl et al., 1987, supra; Moore et al., 1989, supra].

In a preferred embodiment of this invention, the matrix contains TGF-$\beta$ as the proliferation agent and as the chemotactic agent. In particular, TGF-$\beta$I or TGF-$\beta$II may be used as the proliferation and chemotactic agent. Other TGF-$\beta$ forms (e.g., TGF-$\beta$III, TGF-$\beta$IV, TGF-$\beta$V, etc.) or polypeptides having TGF-$\beta$ activity [see Roberts, 1990, supra] may also be useful for this purpose, as well as other forms of this substance to be detected in the future, and other growth factors. For use as the proliferation agent and chemotactic agent, TGF-$\beta$ molecules are dissolved or suspended in the matrix at a concentration of preferably 2–50 ng/ml of matrix solution, and most preferably, 2–10 ng/ml of matrix solution. It will be appreciated that the preferred concentration of TGF-$\beta$ that will stimulate proliferation of repair cells may vary with the particular animal to be treated.

A transforming factor or factors may also be present in the matrix solution so that after repair cells have populated the matrix, the transforming factor will be released into the defect site in a concentration sufficient to promote differentiation (i.e., transformation) of the repair cells into chondrocytes which form new stable cartilage tissue. Proper timing of the release of the transforming factor is particularly important if the transforming factor can inhibit or interfere with the effectiveness of the proliferation agent [see Roberts et al. (1990), supra].

Transforming factors useful in the compositions and methods of this invention include any peptide, polypeptide, protein or any other compound or composition which induces differentiation of repair cells into chondrocytes which produce cartilage-specific proteoglycans and type II collagen. The ability of a compound or composition to induce or stimulate production of cartilage-specific proteoglycans and type II collagen in cells can be determined using assays known in the art [e.g., Seyedin et al., 1985, supra; Seyedin et al., 1987, supra]. The transforming factors useful in the compositions and methods of this invention include, for example, TGF-$\beta$s, TGF-$\alpha$s and FGFs (acid or basic). These transforming factors may be used singly or in combination. In addition, TGF-$\beta$ may be used in combination with EGF.

The properly timed release of the transforming factor may be achieved by packaging the transforming factor in or with an appropriate delivery system. Delivery systems useful in the compositions and methods of this invention include liposomes, bioerodible polymers, carbohydrate-based corpuscles, fibers such as collagen which are chemically linked to heparin sulfate proteoglycans or other such molecules to which transforming factors bind spontaneously, and osmotic pumps. Delivery systems such as liposomes, bioerodible polymers, fibers with bound transforming factors and carbohydrate-based corpuscles containing the transforming agent may be mixed with the matrix solution used to fill the defect. These systems are known and available in the art [see P. Johnson and J. G. Lloyd-Jones, eds., *Drug Delivery Systems* (Chichester, England: Ellis Horwood Ltd., 1987)]. Liposomes may be prepared according to the procedure of Kim et al., *Biochem. Biophys.*

*Acta.* 728, pp. 339–348 (1983). Other liposome preparation procedures may also be used. Additional factors for stimulating chondrocytes to synthesize the cartilage tissue components may b included with the transforming factor in the delivery system.

In a preferred embodiment of this invention, the matrix contains TGF-$\beta$ as the proliferation and chemotactic agent, and contains TGF-$\beta$ packaged in a delivery system as the transforming factor. In particular, TGF-$\beta$I or TGF-$\beta$II may be used as the proliferation and chemotactic agent and as the transforming factor. Other TGF-$\beta$ forms (e.g., TGF-$\beta$III, TGF-$\beta$IV, TGF-$\beta$V, etc.) or polypeptides having TGF-$\beta$ activity (see Roberts, 1990, supra) may also be useful for this purpose, as well as other forms of this substance to be detected in the future, and other growth factors.

In a preferred embodiment, a TGF-$\beta$ concentration of preferably 2–50 ng/ml of matrix solution, and most preferably, 2–10 ng/ml of matrix solution, is used as a proliferation agent and as a chemotactic agent. A substantially higher concentration of TGF-$\beta$ is also present in a subsequently releasable form in the matrix composition as a transforming factor. Preferably, the subsequent concentration of TGF-$\beta$ is greater than 200 ng/ml of matrix and, most preferably, is greater than 500 ng/ml of matrix. It will be appreciated that the preferred concentration of TGF-$\beta$ to induce differentiation of repair cells may vary with the particular animal to be treated.

It is necessary to stagger the exposure of the repair cells to the two concentration ranges of TGF-$\beta$, since TGF-$\beta$ at relatively high concentrations (e.g., greater than 200 ng/ml of matrix solution) may not only transform repair cells into chondrocytes, but also will inhibit chemotactic attraction of repair cells; whereas at relatively low concentrations (e.g., 2–10 ng/ml), TGF-$\beta$ attracts repair cells and stimulates their proliferation, but will not induce transformation of repair cells into chondrocytes which produce cartilage tissue.

In a preferred embodiment of this invention, in order to obtain the sequence of chemotaxis and proliferation, followed by transformation, TGF-$\beta$ is present both in a free, unencapsulated form and in an encapsulated, or otherwise sequestered, form in the matrix. Preferably, for the purpose of attracting and inducing proliferation of repair cells in the matrix and defect area, TGF-$\beta$ molecules are dissolved or suspended in the matrix at a concentration of 2–10 ng/ml of matrix solution. To promote transformation of repair cells in the matrix into chondrocytes, TGF-$\beta$ molecules are also present in the matrix sequestered in multivesicular liposomes according to the method of Kim et al., 1983, supra, at a concentration of greater than 200 ng/ml of matrix solution, and preferably at a concentration of greater than 500 ng/ml. The TGF-$\beta$-loaded liposomes are disrupted when the attracted repair cells have populated the matrix and have started to degrade the matrix. During the degradation of the matrix, the repair cells ingest and/or degrade the liposomes, resulting in the release of TGF-$\beta$ at concentrations sufficient to induce the transformation of repair cells into chondrocytes.

The required two-stage delivery of chemotactic and proliferating versus transforming concentrations of TGF-$\beta$ may also be achieved by combining transforming concentrations of TGF-$\beta$ with a bioerodible polymer. Alternatively, a pump, and preferably an implanted osmotic pump, may be used to control the concentration of TGF-$\beta$ in the defect and matrix. In this embodiment of the invention, the pump controls the concentration of TGF-$\beta$ in the matrix, i.e., the pump may release TGF-$\beta$ at an initial chemotactic and proliferation stimulating concentration and at a subsequent transforming concentration. Preferably, the transforming concentration of TGF-$\beta$ is delivered by the pump approximately 1 to 2 weeks post-operatively. Delivery of the transforming factor into the defect volume is preferably localized to the matrix in the defect site.

The proliferation agents and, when used, the transforming factors in the compositions of this invention are applied in the defect site within the biodegradable matrix. Their presence is thus restricted to a very localized site. This is done to avoid their free injection or infusion into a joint space. Such free infusion may produce the adverse effect of stimulating the cells of the synovial membrane to produce joint effusion.

Fibronectin or any other compound, including peptides as small as tetrapeptides, that contain the amino acid sequence Arg-Gly-Asp, may be used as cell adhesion promoting factors [Ruoslathi et al., 1986, supra] in order to enhance the initial adhesion of repair cells to the matrix deposited in the defect site. Fibrin and certain collagen matrices already contain this sequence [Ruoslathi et al., 1986,supra]. When other biodegradable matrices are used, such cell adhesion promoting factors may be mixed with the matrix material before the matrix is used to dress the defect. Peptides containing Arg-Gly-Asp may also be chemically coupled to the matrix material (e.g., to its fibers or meshes) or to a compound added to the matrix, such as albumin.

The compositions hereinbefore described are useful in methods to induce cartilage formation at a selected site of defect or lesion in cartilage tissue of an animal.

The methods of this invention allow for a treatment of cartilage defects in animals, including humans, that is simple to administer and is restricted in location to the affected joint area. The entire treatment may be carried out in a single arthroscopic or open surgical procedure.

To carry out the methods of treating defects or lesions in cartilage according to this invention, a defect or lesion is identified, prepared, and dressed with a biodegradable matrix composition according to this invention. A proliferation (mitogenic) agent is present in the matrix composition at an appropriate concentration to stimulate the proliferation of repair cells in the matrix and defect or lesion. The same agent may also, at this concentration, serve as a chemotactic agent to attract repair cells, provided that the factor used has a combined effect with respect to cell proliferation and chemotaxis (as does TGF-$\beta$ at 2–10 ng/ml of matrix). Alternatively, two different agents may be present in the matrix, one with a specific proliferative effect, and the other with a specific chemotactic effect. In an alternative embodiment, after the defect area is dressed with the biodegradable matrix, the proliferation agent and, if desired, a chemotactic agent, may be injected directly into the matrix-filled defect area.

In a subsequent step, the repair cells in the matrix are exposed to a transforming factor at the appropriate time at a concentration sufficient to transform the repair cells into chondrocytes which produce stable cartilage tissue. This may be accomplished by including an appropriate delivery system containing the transforming factor within the matrix composition as described above. Alternatively, the transforming agent may be delivered by injection directly into the matrix-filled defect area at the appropriate time. The transforming concentration should be made available to the cells approximately 1 to 2 weeks following the initial implantation of the biodegradable matrix into the defect area. Additional factors may be added to the delivery system or directly injected in order to better promote synthesis of the cartilage matrix components at this time point.

Cartilage defects or lesions in animals are readily identifiable visually during arthroscopic examination of the joint or during simple examination of the lesion or defect during open surgery. Cartilage defects may also be identified inferentially by using computer aided tomography (CAT scanning), X-ray examination, magnetic resonance imaging (MRI), analysis of synovial fluid or serum markers, or by any other procedure known in the art.

Once a defect has been identified, the surgeon may elect to surgically modify the defect to enhance the ability of the defect to physically retain the solutions and matrix material that are added in the treatment methods described herein. Preferably, instead of having a flat or shallow concave geometry, the defect has or is shaped to have vertical edges or is undercut in order to better retain the solutions and matrix materials added in the treatment methods described herein.

In addition to the above mechanical measures, which will improve matrix adherence to the defect site, chemical measures may also enhance matrix adhesion. Such measures include degrading the superficial layers of cartilage proteoglycans on the defect surface to expose the collagen fibrils of the cartilage so that they may interact with the collagen fibrils of the matrix (when a collagenous matrix is used) or with the fibrin fibrils of the matrix (when a fibrin matrix is used). The proteoglycans on the surface of the cartilage not only tend to interfere with adherence of a fibrin or other biodegradable matrix to the cartilage, but also inhibit thrombin activity locally. Advantageously, proteoglycan degradation products may also have a chemotactic effect on repair cells [Moore, A.R. et al., *Int. J. Tiss. Reac.*, XI(6), pp. 301–307 (1989)].

Furthermore, the adhesion of the matrix to the cartilage of the defect can also be enhanced by using fibrin glue (i.e., blood factor XIII or fibrin stabilization factor) to promote chemical bonding (cross-linking) of the fibrils of the matrix to the cartilage collagen fibrils on the defect surface [see Gibble et al., *Transfusion*. 30(8), pp. 741–47 (1990)]. The enzyme transglutaminase may be used to the same effect [see, e.g., Ichinose et al., *J. Biol. Chem.*, 265(23), pp. 13411-14 (1990); "Transglutaminase," Eds: V. A. Najjar and L. Lorand, Martinus Nijhoff Publishers (Boston, 1984)]. Other compounds that can promote adhesion of extracellular materials may also be used.

According to one embodiment of the methods of this invention, the surface of the defect is dried by blotting the area using sterile absorbent tissue, and the defect volume is filled with a sterile enzyme solution for a period of 2–10 minutes to degrade the proteoglycans present on the surface of the cartilage and locally within approximately 1 to 2 $\mu$m deep from the surface of the defect. Various enzymes may be used, singly or in combination, in sterile buffered aqueous solutions to degrade the proteoglycans. The pH of the solution should be adjusted to optimize enzyme activity.

Enzymes useful to degrade the proteoglycans in the methods of this invention include chondroitinase ABC, chondroitinase AC, hyaluronidase, pepsin, trypsin, chymotrypsin, papain, pronase, stromelysin and Staph V8 protease. The appropriate concentration of a particular enzyme or combination of enzymes will depend on the activity of the enzyme solution.

In a preferred embodiment of this invention, the defect is filled with a sterile solution of chondroitinase ABC at a concentration of I U/ml and digestion is allowed to proceed for 4 minutes. The preferred concentration of chondroitinase ABC was determined by examining with an electron microscope rabbit joint cartilage tissue which had been treated with various concentrations of enzyme for various periods of time as described in Example 1. Any other enzyme used should be employed at a concentration for a time period such that only superficial proteoglycans down to a depth of about 1–2 $\mu$m are degraded.

The amount of time the enzyme solution is applied should be kept to a minimum to effect the degradation of the proteoglycans predominantly in the repair area. For chondroitinase ABC at a concentration of 1 U/ml, a digestion period longer than 10 minutes may result in the unnecessary and potentially harmful degradation of th proteoglycans outside the defect area. Furthermore, digestion times longer than 10 minutes contribute excessively to the overall time of the procedure. The overall time of the procedure should be kept to a minimum, especially during open arthrotomy, because cartilage may be damaged by exposure to air [Mitchell et al., (1989), supra]. For these reasons, in the embodiments of the methods of this invention that include the step of degradation of proteoglycans by enzymatic digestion, digestion times of less than 10 minutes are preferred and digestion times of less than 5 minutes are most preferred.

According to the methods of this invention, after the enzyme has degraded the proteoglycans from the surface of the defect, the enzyme solution should be removed from the defect area. Removal of the enzyme solution may be effected by using an aspirator equipped with a fine suction tip followed by sponging with cottonoid. Alternatively, the enzyme solution may be removed by sponging up with cottonoid alone.

Following removal of the enzyme solution, the defect should be rinsed thoroughly, preferably three times, with sterile physiologic saline (e.g., 0.15 M NaCl). The rinsed defect site should then be dried. Sterile gauze or cottonoid may be used to dry the defect site.

Alternatively, or in addition to the enzyme treatment step, the defect site may be dressed with a compound, such as fibrin glue or transglutaminase, to enhance adhesion of the matrix to the defect site. In a preferred embodiment, fibrin glue or transglutaminase is applied to the defect site after the defect site has been rinsed and dried following enzyme treatment.

According to the methods of this invention, the defect site is next dressed with a composition of this invention, described herein, to fill the defect preferably to its edges with the matrix composition such that a flat plane is formed. The composition comprises a matrix material and a proliferation agent and, if desired, a chemotactic agent. The composition used in this step may also contain, packaged in an appropriate delivery system, a transforming factor. In the most preferred method of the invention, the matrix contains a proliferation agent, a chemotactic agent (which may be identical to the proliferation agent) and a transforming factor which is packaged in or associated with a delivery system that releases the transforming factor, at a time that the repair cells populating the matrix have begun remodelling the intercellular substance, at a concentration that transforms the repair cells into chondrocytes. Preferred compositions are described above.

If the matrix does not contain proliferation and chemotactic agent(s), the agent(s) may be injected directly into the matrix-filled defect area in order to deliver the preferred concentrations to promote chemotaxis and proliferation of repair cells. Preferably, in this embodiment of the invention, after dressing the defect with the matrix, TGF-$\beta$ is injected locally into the matrix to give a concentration of 2-10 ng/ml of matrix. Injection should be localized to the matrix-filled defect area to avoid exposure of cells of the synovial membrane to growth factors which could lead to cell proliferation and joint effusion.

After the defect site is dressed with the matrix composition (and, in the case of fibrin matrices, once the matrix has solidified) and, if required, the proliferation agent has been injected into the matrix-filled defect site, the joint capsule and skin incisions may be closed and the arthroscopy or open surgery terminated.

If the transforming factor is not present in the matrix in an appropriate delivery system, the transforming factor may be added directly into the matrix approximately 1-2 weeks postoperatively, for example, by injection or by an osmotic pump, at a concentration sufficient to transform repair cells into chondrocytes. Preferably, in this embodiment of the invention, TGF-B is added directly into the matrix approximately one week post-operatively to give a concentration of greater than 200 ng/ml, and most preferably greater than 500 ng/ml of matrix.

The methods described herein for repairing defects in articular cartilage are most effective when the defect does not extend to the bone beneath the cartilage. The methods described herein may also be used for repairing defects in meniscal cartilage tissue.

In order that the invention described herein may be more fully understood, the following examples are set forth. It should be understood that these examples are for illustrative purposes and are not to be construed as limiting this invention in any manner.

EXAMPLE 1

Enzyme Testing for Proteglycan Removal

In order to promote and improve matrix adherence along superficial defect surfaces of articular cartilage tissue, proteoglycan molecules within the superficial cartilage matrix may be removed enzymatically, in order to expose the collagen fibrillar network to externally applied matrices and to migrating repair cells. Various proteases and glycosaminoglycan-degrading enzymes are suitable to be used for this purpose, but pH conditions should be controlled to provide maximal activity for each enzyme.

In this example, we tested chondroitinase ABC (0.5-5 U/ml) and trypsin (0.5-4%) for their ability to effect proteoglycan removal. Knee joints from freshly slaughtered rabbits, obtained from a local butcher, were employed. Mechanically-created superficial cartilage defects were exposed to the enzyme solutions for a period of 4 minutes. Solutions were then removed with absorbent tissue and the defect sites rinsed thoroughly with physiologic saline. Following this procedure, cartilage tissue was fixed immediately in 2% (v/v) glutaraldehyde solution (buffered with 0.05M sodium cacodylate, pH 7.4) containing 0.7% (w/v) ruthenium hexamine trichloride (RHT) for histological examination. The post-fixation medium consisted of a 1% RHT-osmium tetroxide solution (buffered with 0.1M sodium cacodylate). Tissue was dehydrated in a graded series of ethanol and embedded in Epon 812. Thin sections were cut, stained with uranyl acetate and lead citrate, and examined in an electron microscope. In these sections, RHT-fixed (i.e., precipitated) proteoglycans appeared as darkly-staining granules. Enzyme concentrations removing a superficial layer of proteoglycans no more than 1-2 $\mu$m in thickness were defined as optimal (deeper penetration of enzymes could affect the underlying chondrocytes). Chondroitinase ABC was found to be optimally active at a concentration of approximately 1 U/ml. Trypsin was found to be optimally active at a concentration of approximately 2.5%. The optimal activity range for other glycosaminoglycanases or proteases may be determined in a similar manner. Any buffer may be used in conjunction with the enzyme provided that it is nontoxic and that its maximal buffering capacity occurs at a pH value close to that required for maximal enzyme activity.

EXAMPLE 2

Matrix Adherence to Superficial Defects

The possibility of promoting matrix adhesion along defect surfaces by controlled enzyme digestion of superficial cartilage proteoglycans was investigated. Defects were created in the knee joints of three mature rabbits by cutting with a planing knife. These defects were not enzyme treated. The defects were filled with a fibrin matrix, formed by mixing 20 $\mu$l of a thrombin solution (100 U/ml aqueous buffer) with each ml of fibrinogen solution (1 mg/ml aqueous buffer) approximately 200 second before filling the defect. The rabbits were sacrificed after I month and the knee joints examined to determine the extent to which the fibrin matrix had adhered to the defect site. The results were compared to those achieved in rabbits whose defects had been treated with chondroitinase ABC (1 U/ml for 4 minutes) before the defect was filled with fibrin matrix (see Examples 3, 4 and 5).

The fibrin matrices deposited in defect areas left untreated with an enzyme exhibited low affinity to adhere to the defect surface. Following enzyme treatment, the sticking capacity of the fibrin matrices (determined indirectly by measuring mechanical strength to adhere, i.e., by testing the easiness with which the matrix could be pushed away manually with the tip of a forceps, and indirectly by noting the number of defects in which the matrix successfully remained sticking throughout the experiment) was significantly increased. The low affinity of matrices for the defect surfaces in the absence of enzyme treatment probably is due to a local inhibition of matrix adhesion by proteoglycan molecules and an inhibition of fibrin polymerization. Both of these effects are prevented by enzymatic removal of superficial proteoglycans along the defect surface area.

EXAMPLE 3

Application of Growth Factors to Defect Sites to Provide Chemotactic Stimulation of Repair Cell Migration into Defect Areas and Induction of Repair Cell Proliferation Various growth factors were tested for their usefulness in stimulating chemotactic migration of repair cells to the defect area in order to accomplish healing of the defect.

The growth factors employed included a) epidermal growth factor (EGF), b) basic fibroblast growth factor (bFGF), c) insulin-like growth factor I (IGF I), d) human growth hormone (hGH) and e) transforming growth factor-$\beta$ (TGF-$\beta$) at concentrations of between 5-10 ng/ml.

Each of these factors was applied locally to defects produced in the knee following chondroitinase ABC treatment and rinsing as described in Example 2. A total of ten animals (two per growth factor) were utilized. Each growth factor was able to chemotactically attract or locally stimulate proliferation of repair cells to the defect surfaces sufficiently to completely cover the defect surfaces. However, the cells were only present on the surfaces of the defects, and in no instance was proliferation of the repair cells adequate to fill the defect volume.

(It is believed that the proteoglycan degradation products by themselves, i.e., without the addition of any other agent, exert a sufficient chemotactic effect to attract repair cells to the defect. Moore, A.R. et al. [Int. J. Tiss. Reac., XI(b). pp. 301-107, 1989] have shown that proteoglycan degradation products have chemotactic effects per se.)

EXAMPLE 4

Application to Defect Sites of Growth Factors Entrapped in Biodegradable Matrices to Provide Chemotactic Stimulation of Repair Cell Migration into Defect Areas and Induction of Repair Cell Proliferation Since local application of a growth factor under the conditions of Example 3 in no instance induces repair cell proliferation adequate to fill the defect volume, the experiment was repeated using the same growth factors, but this time the growth factors were entrapped in biodegradable matrices. The biodegradable matrices used were fibrin, collagen and Sepharose. Sufficient quantities of matrices containing growth factor were applied to fill the defect volumes completely.

Fibrin matrices were formed by mixing 20 $\mu$l of a thrombin solution (100 U/ml of an aqueous buffer solution: Veronal acetate buffer, pH 7.0) with each ml of fibrinogen solution (1 mg/ml of an aqueous buffer solution: 0.05M Tris, pH 7.4, 0.1M NaCl) approximately 200 seconds prior to filling the defect. For collagen matrices, sufficiently viscous solutions were made using Colagen-Vliess ® or gelatine-blood-mixtures. For Sepharose matrices, defects were filled with liquid solutions of Sepharose at 39-42° C. Upon cooling (35-38° C.), a Sepharose matrix was formed in the defect.

Thirty rabbits (two for each type of matrix and growth factor) were utilized for this experiment. In all cases where the deposited matrix remained adherent to the defect, it became completely populated by fibroblast-like repair cells. This situation was found to exist as early as eight to ten days post-operatively. No further changes occurred in the structural organization of the repair tissue up to four weeks post-operatively, except that the biodegradable matrices became remodelled by the repair cells and replaced by a loose, connective tissue type of extracellular matrix.

Transformation of this tissue to cartilage tissue did not occur.

EXAMPLE 5

Application to Defect Sites of Growth Factors Entrapped in Biodegradable Matrices to Provide Chemotactic Stimulation of Repair Cell Migration into Defect Areas and Induction of Repair Cell Proliferation Followed by Timed, Local Release of a Transforming Factor at a Secondary Stage to Provide Transformation of the Defect Site into Hyaline Cartilace The observation that matrices within the defect volume were completely filled with repair cells following application of growth factor, and that these cells were able to remodel the deposited matrix (see Example 4), prompted the investigation of the effects of introducing a transforming factor (such as TGF-$\beta$) in an encapsulated form (e.g., liposomes) from which the transforming factor would be released when the matrix was completely populated with repair cells that had begun to remodel the intercellular structure.

TGF-$\beta$ was mixed into the fibrinogen solution (1 mg/ml) at a low concentration (e.g., 2-10 ng/ml) for the purpose of promoting the initial chemotactic and proliferative effects. TGF-$\beta$ was also encapsulated in liposomes according to the method of Kim et al. (1983) supra. These TGF-$\beta$ containing liposomes were added to the same fibrinogen solution in a concentration adequate to provide, when the liposomes were ruptured and the TGF-$\beta$ was released, the higher concentration of 100-1000 ng of TGF-$\beta$ per ml of fibrinogen for the purpose of promoting transformation of the repair cells into chondrocytes and transformation of the matrix-filled defect into cartilage during a secondary stage when the repair cells populating the fibrin matrix have begun to remodel the intercellular substance.

Ten mature rabbits, in which superficial knee joint articular cartilage defects were produced as in Example 2, were treated by application of this mixture of fibrinogen containing free and liposome-encapsulated TGF-$\beta$ to the defect site. In the various experiments in this series of experiments, the concentration of free TGF-$\beta$ was maintained in the range from 2-10 ng/ml of fibrinogen while the concentration of encapsulated TGF-$\beta$ was varied to provide (upon release of the TGF-$\beta$ from the liposomes) a concentration between 100 and 1000 ng TGF-$\beta$/ml fibrinogen in 100 ng steps. Formation of hyaline cartilage tissue occurred at the treatment sites in all cases. The most reproducible results were obtained at concentrations of above 200 ng encapsulated TGF-$\beta$/ml fibrinogen solution, and preferably above 500 ng TGF-$\beta$/ml of fibrinogen solution.

EXAMPLE 6

Determination of the Time Point of Tissue Transformation

In this experiment, a group of six mature rabbits were subjected to knee surgery to produce superficial defects as in Example 2. A full treatment scheme for superficial defect repair was applied, i.e., treatment with chondroitinase ABC (1 U/ml for 4 minutes), followed by filling the defect site with fibrin matrix (1 mg/ml fibrinogen solution, 20 $\mu$l 100 U/ml thrombin solution per ml of fibrinogen solution) containing free TGF-$\beta$ ($\sim$2-10 ng/ml) and liposome encapsulated TGF-β (~800 ng/ml). Three rabbits were sacrificed at eight, ten and twelve days postoperatively, the remaining three at twenty, twenty-four and twenty-eight days. Transformation of the primitive, fibroblast-like repair cell tissue into hyaline cartilage tissue occurred between days twelve and twenty in this animal model. This was determined on the basis of histological examination. At days eight to twelve, loose fibrous repair tissue was still present (the applied fibrin matrix being partially or completely remodelled), whereas at day twenty and subsequently, the defect space was partially or completely filled with hyaline cartilage tissue.

EXAMPLE 7

Application of Cartilage Repair Procedures in a Mini-pig Model

The experimental procedures utilized in the rabbit model, supra, were applied to a larger animal model, the mini-pig. Superficial defects (0.6 mm wide, 0.6 mm deep and approximately 10–15 mm long) were created in four mature mini-pigs (2–4 years old, 80–110 lbs.) by cutting with a planing knife in the patellar groove and on the medial condyle. The defects were then treated with chondroitinase ABC (1 U/ml for 4 minutes, as used for rabbits, supra). The enzyme solution was removed, the defect dried, rinsed with physiological saline, then dried again. The defect sites were then filled with a fibrinogen matrix solution. The fibrinogen matrix solution used in this experiment contained 2–6 ng of free TGF-β per ml, and 1500–2000 ng of liposome-encapsulated TGF-β per ml of fibrinogen solution. Prior to filling the defects, thrombin was added to the matrix solution as described above in the rabbit experiment.

The mini-pigs were sacrificed 6 weeks postoperatively, and the sites of the matrix-filled defects were examined histologically. All sites showed healing, i.e., formation of hyaline cartilage tissue at the treatment site.

I claim:

1. A method of inducing cartilage formation at a selected site in the cartilage tissue of an animal comprising dressing the site with a composition comprising:
   a biodegradable matrix or matrix-forming material,
   a proliferation agent at an appropriate concentration in the matrix or matrix-forming material to stimulate the proliferation of repair cells in the matrix, and
   a transforming factor associated with a delivery system in the matrix or matrix-forming material and at an appropriate concentration such that upon subsequent delivery of the transforming factor to repair cells in the matrix, the repair cells are transformed into chondrocytes that produce cartilage tissue.

2. A method according to claim 1 for inducing cartilage formation at a selected site in the cartilage tissue of an animal comprising dressing the site with a composition comprising:
   a fibrin matrix formed by adding thrombin to a fibrinogen solution,
   TGF-β present at a concentration of 2–10 ng/ml of fibrinogen solution, and
   TGF-β encapsulated in liposomes and present at a concentration of greater than 200 ng/ml of fibrinogen solution.

3. A method for treating defects or lesions in cartilage in animals which comprises:
   filling the defect with a biodegradable matrix containing an effective amount of a proliferation agent to stimulate proliferation of repair cells, an effective amount of a chemotactic agent to attract repair cells to the matrix and defect, and an effective amount of a transforming factor associated with a delivery system for subsequent delivery to transform repair cells into chondrocytes.

4. A method for treating defects or lesions at a selected site in cartilage in animals which comprises:
   filling the defect or lesion with a biodegradable matrix containing an effective amount of a chemotactic agent to attract repair cells to the matrix and defect or lesion and an effective amount of a proliferation agent to stimulate proliferation of repair cells,
   and delivering a transforming factor into the matrix, approximately 1–2 weeks after filling the defect with the matrix, at a concentration sufficient to transform repair cells into chondrocytes.

5. The method according to claim 3 or 4 further comprising the step of covering the surface of the defect with fibrin glue or transglutaminase prior to filling the defect with the biodegradable matrix.

6. A method for treating defects or lesions in cartilage in animals which comprises:
   filling the defect with an agent to remove proteoglycan from the surface of the defect,
   removing the agent, and
   dressing the defect with a biodegradable matrix containing an effective amount of a proliferation agent to stimulate proliferation of repair cells and containing a transforming factor associated with a delivery system that subsequently releases the transforming factor at a concentration sufficient to transform repair cells into chondrocytes.

7. A method for treating defects or lesions in cartilage in animals which comprises:
   filling the defect with an agent to remove proteoglycan from the surface of the defect,
   removing the agent,
   dressing the defect with a biodegradable matrix containing an effective amount of a proliferation agent to stimulate proliferation of repair cells, and
   delivering a transforming factor into the matrix approximately 1–2 weeks after filling the defect, at a concentration sufficient to transform repair cells into chondrocytes.

8. The method according to claim 6 or 7 further comprising the step of covering the surface of the defect or lesion with fibrin glue or transglutaminase prior to dressing the defect or lesion with the biodegradable matrix.

9. The method according to claim 6 or 7 wherein the biodegradable matrix also contains a chemotactic agent at a concentration sufficient to attract repair cells to the matrix and area of the defect or lesion in cartilage.

10. The method of claim 6 or 7 in which the agent to remove proteoglycan from the surface of the defect is selected from the group consisting of chondroitinase ABC, chondroitinase AC, hyaluronidase, pepsin, papain, trypsin, chymotrypsin, pronase, stromelysin and Staph V8 protease.

11. The method of claim 9 wherein the proliferation agent, the chemotactic agent, and the transforming factor are TGF-β.

12. The method of claim 3 or 6 in which the delivery system for the delivery of the transforming factor is selected from the group consisting of liposomes, bioerodible polymers, collagen fibers chemically linked to heparin sulfate proteoglycans, and carbohydrate-based corpuscles.

13. The method of claim 3, 4, 6 or 7 in which the biodegradable matrix is selected from the group consisting of fibrin, collagen, gelatin, Sepharose or combinations thereof.

14. The method according to claim 3, 4, 6 or 7 wherein the biodegradable matrix is fibrin which is formed by addition of thrombin to a solution of fibrinogen immediately before filling the defect or lesion with the fibrinogen solution.

15. The method according to claim 9 wherein the proliferation agent and the chemotactic agent is TGF-$\beta$ at a concentration of 2-10 ng/ml of matrix, and the transforming factor is TGF-$\beta$ encapsulated in liposomes and present at a concentration of greater than 200 ng/ml of matrix.

16. The method according to claim 6 or 7 wherein the agent to remove proteoglycan from the surface of the defect is chondroitinase ABC, and the defect is filled for 4 minutes with a solution comprising chondroitinase ABC at a concentration of 1 unit/ml.

17. The method according to claim 3, 4, 6 or 7 wherein the biodegradable matrix further contains a cell adhesion promoting factor comprising the tripeptide Arg-Gly-Asp.

18. A method for treating defects or lesions in cartilage in animals which comprises:
   filling the defect or lesion area with a sterile solution of chondroitinase ABC at a concentration of 1 unit/ml for 4 minutes,
   removing the solution of chondroitinase ABC,
   rinsing the defect area with sterile physiologic saline,
   drying the defect area,
   adding 2 units of thrombin to each ml of a matrix-forming solution comprising 1 mg/ml of fibrinogen, and containing TGF-$\beta$ a concentration of 2-10 ng/ml, and TGF-$\beta$ in liposomes for subsequent delivery at a concentration greater than 200 ng/ml, and
   filling the defect with the matrix-forming solution immediately after addition of the thrombin.

19. The method according to claim 18 further comprising the step of covering the surface of the defect with fibrin glue or transglutaminase prior to filling the defect with the matrix-forming solution.

20. The method according to claim 18 wherein the TGF-$\beta$ in liposomes is at a concentration of greater than 500 ng/ml.

21. The method according to claim 3, wherein the composition further comprises a chemotactic agent at an appropriate concentration in the matrix or matrix-forming material to attract repair cells to the selected site in the cartilage tissue.

22. The method according to claim 6 or 7, wherein the cartilage tissue to be treated is meniscal cartilage.

23. The method according to any one of claims 3 or 4, wherein the proliferation agent, the chemotactic agent, and the transforming factor are TGF-$\beta$.

24. The method according to claim 3, wherein the proliferation agent and the chemotactic agent are TGF-$\beta$ at a concentration of 2-10 ng/ml of matrix, and the transforming factor at TGF-$\beta$ encapsulated in liposomes and present at a concentration of greater than 200 ng/ml of matrix.

* * * * *

UNITED STATES PATENT AND TRADEMARK OFFICE
CERTIFICATE OF CORRECTION

PATENT NO. : 5,206,023  Page 1 of 3
DATED : April 27, 1993
INVENTOR(S) : Hunziker, Ernst It is certified that error appears in the above-indentified patent and that said Letters Patent is hereby corrected as shown below:

Cover page, Item [54] line 1, and

Col. 1, line 1, "METHOD" should be --METHODS--.

Page 2, Item [56] References Cited

OTHER PUBLICATIONS

Col. 1, line 34, "Conrolled" should be --Controlled--.

Col. 2, line 11, "351" should be --251--;

line 35, "Chemisry" should be --Chemistry--.

Col. 1, line 1, "METHOD" should be --METHODS--.

Col. 2, line 22, "Lippncott" should be --Lippincott--;

line 54, "(TGF-B)" should be --(TGF-$\beta$)--.

Col. 4, line 27, "tempo" should be --temporo--;

line 61, After "supra" delete "1" and insert a bracket therefor --]--.

Col. 5, line 54, After "supra" delete "1" and insert a bracket therefor --]--.

UNITED STATES PATENT AND TRADEMARK OFFICE
CERTIFICATE OF CORRECTION

PATENT NO. : 5,206,023
DATED : April 27, 1993
INVENTOR(S) : Hunziker, Ernst

It is certified that error appears in the above-indentified patent and that said Letters Patent is hereby corrected as shown below:

Col. 7, line 64, "TGF-Bs" should be --TGF-βs--.

Col. 9, line 4, "b" should be --be--.

Col. 13, line 27, "TGF-B" should be --TGF-β--;

line 44, "Proteglycan" should be --Proteoglycan--.

Col. 14 line 34, "second" should be --seconds--;

line 35, Change "I" to --1--.

Col. 16, line 14, "Hvaline" should be --Hyalene--;

line 14, "Cartilace" should be --Cartilage--.

UNITED STATES PATENT AND TRADEMARK OFFICE
CERTIFICATE OF CORRECTION

PATENT NO. : 5,206,023
DATED : April 27, 1993
INVENTOR(S) : Hunziker, Ernst

It is certified that error appears in the above-indentified patent and that said Letters Patent is hereby corrected as shown below:

Col. 20, line 5, After "TGF-B" insert --at--.

Signed and Sealed this

Twenty-second Day of November, 1994

Attest:

BRUCE LEHMAN

Attesting Officer    Commissioner of Patents and Trademarks